United States Patent [19]
Anderson et al.

[11] Patent Number: 6,127,165
[45] Date of Patent: Oct. 3, 2000

[54] RAT GLUTATHIONE SYNTHETASE GENE

[75] Inventors: Mary Elizabeth Anderson; Chin-shiou Huang; Alton Meister, all of New York, N.Y.

[73] Assignee: Cornell Research Foundation, Inc., Ithaca, N.Y.

[21] Appl. No.: 08/387,117

[22] Filed: Feb. 13, 1995

[51] Int. Cl.[7] .............................. C12N 1/21; C12N 9/00; C12N 15/63; C07H 21/04
[52] U.S. Cl. ................. 435/252.3; 435/183; 435/254.11; 435/320.1; 536/23.2
[58] Field of Search ........................ 536/23.2; 435/320.1, 435/252.3, 183, 254.11

[56] References Cited

U.S. PATENT DOCUMENTS

| | | | |
|---|---|---|---|
| 4,668,624 | 5/1987 | Roberts | 435/68 |
| 4,879,370 | 11/1989 | Meister | 530/331 |

OTHER PUBLICATIONS

Warner, B. et al. (1993) "Expression of human Mn SOD in Chinese hamster ovary cells confer protection from oxidant injury" Am. J. Phys. 264(6 Pt 1):L598–605, Jun. 1983.

Meister, A., 1985, Glutatione Synthetase from Rat Kidney, *Methods in Enzymology,* 113:393–399.

Moore et al., 1986, Enzymatic synthesis of novel glutathione analogs, *Fed. Proc. Fed. Am. Soc. Exp. BIol.* 45(6):1789.

Snoke, J.E. and Bloch, K., *J. Biol. Chem.* 199:414 (1952).

Snoke, J.E., "Isolation and Properties of Yeast Glutathione Synthetase," *J. Biol. Chem.* 213:813–824 (1955).

Meister, A. in *The Enzynmes* (Boyer, P.D., ed) 3rd Ed. vol. 10, pp. 671–697, Academic Press, N.Y. (1974).

Yan, N. and Meister, A., *J. Biol. Chem.* 265:1588–1593 (1990).

Huang, C.–S., Anderson, M.E., and Meister, a., *J. Biol. Chem.* 268(27):20578–20583 (1993).

Huang, C.–S. Moore, W., and Meister, A., *Proc. Natl. Acad. Sci.,* U.S.A. 85:2464–2468 (1988)

Seelig, G.F., and Meister, A., *Methods in Enzymology* 113, Chapter 47, pp. 379–390 (1985).

Seelig, G.F., and Meister, A., *J. Biol. Chem.* 259:3534–3538 (1984).

Gushima, H., Miya. T., Murata, K., and Kimura, A., *J. Appl. Biochem.* 5:210–218 (1983).

Gushima, H., Yasuda, S., Soeda, E., Yokota, M., Kondo, M. and Kimura, A., *Nucl. Acids Res.* 12(24):9299–9307 (1984).

Mooz, E.D, and Meister, A., "Tripeptide (Glutathione) Synthetase. Purification, Properties, and Mechanism of Action," *Biochemistry,* 6(6):1722–1734 (1967).

Mutoh, N., Nakagawa, C.W., Ando, S., Tanabe, K., and Hayashi, Y., Cloning and Sequencing of the Gene Encoding the Large Subunit of Glutathione Synthetase of Schizosaccharomyces Pombe, *Biochem. Biophys. Res. Comm.* 181(1):430–436 (1991).

Hayashi, Y., Nakagawa, C.W. and Mutoh, N., *Biochem. Cell Biol.,* 69:115–121 (1991).

Grill, E., Loffler, S., Winnacker, E–L. and Zenk, M.H., *Proc. Natl. Acad. Sci. U.S.A.,* 86:6838–6842 (1989).

Habenicht, A., Hille, S., and Knochel, W., "Molecular cloning of the large subunit of glutathione synthetase from *Xenopus laevis* embryos," *Biochem Biophys. Acta* 1174:295–298 (1993).

Oppenheimer, L, Wellner, V., Griffith, O., and Meister, A. (1979) "Glutathione Synthetase Purification From Rat Kidney and Map of the Substrate Binding Sites," *J. Biol. Chem.,* 254(12):5184–5190.

Moore, W.R. et al., "Increased capacity for glutathione synthesis enchances resistance to radiation in *Escherichia coli*:A possible model for mamalian cell protection," *Proc. Natl. Acad. Sci,* USA,86:1461–1464 (1989).

Murata, K., Kimura, A., and Yajima, N., "Glutathione Synthetase of *Aspergillus niger* Structural Properties of the Enzyme in Prokaryotes and Eukaryotes," *Agri. Biol. Chem.* 53(4):1145–1149 (1989).

Nakagawa, C.G., Mutoh, N., and Hayashi, Y., "Glutathione synthetase from the fission yeast. Purfication and its unique heteromeric subunit structure," *Biochem. Cell Biol.* 71:447–453 (1993).

Watanabe, K., Yamano, Y., Murata, K., and Kimyra, A., "Glutathione production by *Escherichia coli* cells with hybrid plasmid containing tandemly polymerized genes for glutatione synthetase," *Appl Microbiol biotechnol* 24:375–378 (1986).

Peters, J.M., Dalrymple, B.P., and Jorgensen, W.K., "Sequence of a Putative Glutatione Synthetase II Gene and Flanking Regions From *Anaplasma Cenrrale,"* *Biochemical and Biophysical Research Communications* 182(3):1040–1046 (1992).

*Primary Examiner*—Kawai Lau
*Attorney, Agent, or Firm*—Pennie & Edmonds LLP

[57] ABSTRACT

The present invention relates to recombinant rat kidney glutathione synthetase. This enzyme can be used to prepare glutathione analogs, and to raise antibodies against glutathione synthetase.

The present invention further relates to a DNA molecule encoding rat kidney glutathione synthetase. The DNA molecule is useful for detecting the presence of the glutathione synthetase gene in animals, and for modifying cell and mammal glutathione production. The DNA molecule can also be used to construct models for evaluation of potential therapies.

20 Claims, 5 Drawing Sheets

Peptide 1   A S Y I L M E K
Peptide 2   S C A A K
Peptide 3   Q L E E L A Q Q A I D R A L A E
Peptide 4   E R N I F D Q R A I E N E L L D R K
Peptide 5   A I E H A D G G V

FIG.1

```
                -34                         -14                    1    6
        TGGAGTTTGAGCTTGGCGAGCAGCTGGACAACGAGCGAGTTGGGATGGCCACCAGCTGGG
                                                        M   A   T   S   W
                 26                          46                   66
        GAAGCATCTTGCAGGATGAGAAGCAGCTGGAAGAGTTGGCACAGCAGGCCATAGACCGGG
         G   S   I   L   Q   D   E   K   Q   L   E   E   L   A   Q   Q   A   I   D   R
                 86                         106                  126
        CCCTGGCTGAGGGGGTGTTGCTGAGGTCCGCAAAGAACCCCAGCTCCTCTGACGTGGTGA
         A   L   A   E   G   V   L   L   R   S   A   K   N   P   S   S   S   D   V   V
                146                         166                  186
        CGTATGCCCCATTCACGCTCTTCCCCTCACCAGTGCCCAGCACTCTGCTGGAGCAGGCCT
         T   Y   A   P   F   T   L   F   P   S   P   V   P   S   T   L   L   E   Q   A
                206                         226                  246
        ATGCTGTGCAGATGGACTTCAACATCCTGGTAGATGCTGTCAGCCAGAACTCCGCCTTCC
         Y   A   V   Q   M   D   F   N   I   L   V   D   A   V   S   Q   N   S   A   F
                266                         286                  306
        TGGAGCAAACACTGTCTAGCACCATCAAAAAGGATGAGTATACTGCCCGTCTCTTTGATA
         L   E   Q   T   L   S   S   T   I   K   K   D   E   Y   T   A   R   L   F   D
                326                         346                  366
        TCTACAAGCAAGTCCTGAAAGAGGGCATAGCCCAGACTGTGTTCCTGGGCCTCAATCGTT
         I   Y   K   Q   V   L   K   E   G   I   A   Q   T   V   F   L   G   L   N*  R
                386                         406                  426
        CAGATTACATGTTCCAGTGCAGCGCAGACGGCTCCAAAGCCCTGAAACAGATTGAGATCA
         S   D   Y   M   F   Q   C   S   A   D   G   S   K   A   L   K   Q   I   E   I
```

FIG. 2A

```
      446                  466                  486
ACACTATCTCTGCCAGCTTTGGGGGCCTGGCCTCCCGGACTCCGGCTGTGCACCGACATG
 N  T  I  S  A  S  F  G  G  L  A  S  R  T  P  A  V  H  R  H 506                  526                  546
TTCTCAATGTCCTGAATAAGACCAACGAAGCTTCCAAGATCCTGTCCAACAACCCCAGCA
 V  L  N  V  L  N* K  T  N  E  A  S  K  I  L  S  N  N  P  S 566                  586                  606
AGGGACTGGCCCTGGGGATCGCCAAAGCCTGGGAGCTCTATGGCTCAGCCAATGCCGTGG
 K  G  L  A  L  G  I  A  K  A  W  E  L  Y  G  S  A  N  A  V 626                  646                  666
TGCTACTGATTGCTCAGGAGAAGGAAAGGAACATATTTGACCAGCGTGCCATAGAGAACG
 V  L  L  I  A  Q  E  K  E  R  N  I  F  D  Q  R  A  I  E  N 686                  706                  726
AGCTGCTAGACAGGAAGATCCATGTAATCCGCCGAAGATTTGAAGATGTCTCTGAAAGGG
 E  L  L  D  R  K  I  H  V  I  R  R  R  F  E  D  V  S  E  R 746                  766                  786
GTTCTCTAGACCAAAACCGAAGGCTGTTTATGGAGGACCAGGAAGTTGCTGTGGTTTACT
 G  S  L  D  Q  N  R  R  L  F  M  E  D  Q  E  V  A  V  V  Y 806                  826                  846
TCCGAGATGGCTACATGCCCAGTCAGTATAACGCACAGAACTGGGAAGCTCGCCTGCTGC
 F  R  D  G  Y  M  P  S  Q  Y  N  A  Q  N  W  E  A  R  L  L 866                  986                  906
TAGAGAGATCATGTGCTGCCAAGTGTCCCGACATTGCCACACAGCTGGCTGGCACTAAGA
 L  E  R  S  C  A  A  K  C  P  D  I  A  T  Q  L  A  G  T  K 926                  946                  966
AGGTGCAGCAGGAACTGAGCAGGGTGGGCCTGCTGGAAGCGCTGCTCCCGGGCCAGCCCG
 K  V  Q  Q  E  L  S  R  V  G  L  L  E  A  L  L  P  G  Q  P
```

FIG. 2B

```
                986                  1006                 1026
AGGCTGTGGCCCGCCTCCGTGCCACCTTTGCTGGCCTCTATTCACTGGACATGGGTGAAG
 E   A   V   A   R   L   R   A   T   F   A   G   L   Y   S   L   D   M   G   E
                1046                 1066                 1086
AAGGGGACCAGGCTGTCGCTGAGGCCCTTGCTGCCCCTAGCCACTTTGTGCTGAAGCCCC
 E   G   D   Q   A   V   A   E   A   L   A   A   P   S   H   F   V   L   K   P
                1106                 1126                 1146
AAAGAGAGGGCGGAGGTAATAACTTCTATGGGGAGGAAATGGTACACGCTCTGGAGCAGC
 Q   R   E   G   G   G   N   N   F   Y   G   E   E   M   V   H   A   L   E   Q
                1166                 1186                 1206
TGAAAGACAGCGAGGAGAGAGCCTCCTACATCCTCATGGAGAAGATTGAACCTGAGCCTT
 L   K   D   S   E   E   R   A   S   Y   I   L   M   E   K   I   E   P   E   P
                1226                 1246                 1266
TTAGGAATTGCTTACTACGGCCTGGCAGCCCTGCCCAAGTGGTCCAGTGCATCTCGGAGC
 F   R   N   C   L   L   R   P   G   S   P   A   Q   V   V   Q   C   I   S   E
                1286                 1306                 1326
TGGGTATTTTTGGAGTCTATGTCAGACAGGGAACAACACTTGTGATGAACAAGCATGTGG
 L   G   I   F   G   V   Y   V   R   Q   G   T   T   L   V   M   N   K   H   V
                1346                 1366                 1386
GGCATCTGCTTCGAACCAAAGCCATTGAACATGCAGATGGAGGTGTGGCAGCAGGAGTGG
 G   H   L   L   R   T   K   A   I   E   H   A   D   G   G   V   A   A   G   V
                1406                 1426                 1446
CAGTCCTGGACAACCCCTACCCTGTGTGAAGACATGTTCTGGGCTTCACTCAAGAGACCT
 A   V   L   D   N   P   Y   P   V   -
                1466                 1486                 1506
TCTATCCTCTGTACTTGGCACTCCTCTCCTGAGGGGCTACCCCTGTACCTGTGTTAGGGG
                1526                 1546                 1566
AGGGAGCTTGTCTCTTTCATAGACCTCCAGGGGCTTTAGGGAAGGGAAAATCCCGGGTCC
```

FIG. 2C

```
                1586                  1606                  1626
CTTCTCTCAGCCTTCCATCCAAGGACCAGAAAAGCTATGATTCCATTGGAAGAGTTCTGG
                1646                  1666                  1686
AGCTCCCCAGATTTGGAGTGGGAATGGAAGCTCCTTTGAGGCAAAGGCCCACAAACCCCA
                1706                  1726                  1746
CACATCTTCATTGCCCTCTCGCCAGCCTTTCCAGCAGGTTCTAGTGCCTTGACCTGGGGT
                1766                  1786                  1806
AGGACCAAGTGACAGGAGGAAGAGGGTAGATGGGCATAGACTTCCCCAGCTCTGCCCTAA
                1826                  1846
ATAAAACAATGCTGATTCAATGAAAAAAAAAAAAAAAAAAAAAAAA
```

FIG. 2D

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
      (A) LENGTH: 8 amino acids
      (B) TYPE: amino acid
      (D) TOPOLOGY: linear (ii) MOLECULE TYPE: peptide (v) FRAGMENT TYPE: internal (xi) SEQUENCE DESCRIPTION: SEQ ID NO:1:

Ala Ser Tyr Ile Leu Met Glu Lys
1             5

(2) INFORMATION FOR SEQ ID NO:2:

(i) SEQUENCE CHARACTERISTICS:
      (A) LENGTH: 5 amino acids
      (B) TYPE: amino acid
      (D) TOPOLOGY: linear

```
        (ii) MOLECULE TYPE: peptide (v) FRAGMENT TYPE: internal (xi) SEQUENCE DESCRIPTION: SEQ ID NO:2:

Ser Cys Ala Ala Lys
1               5

(2) INFORMATION FOR SEQ ID NO:3:

(i) SEQUENCE CHARACTERISTICS:
             (A) LENGTH: 16 amino acids
             (B) TYPE: amino acid
             (D) TOPOLOGY: linear (ii) MOLECULE TYPE: peptide (v) FRAGMENT TYPE: internal (xi) SEQUENCE DESCRIPTION: SEQ ID NO:3:

Gln Leu Glu Glu Leu Ala Gln Gln Ala Ile Asp Arg Ala Leu Ala Glu
1               5                  10                  15

(2) INFORMATION FOR SEQ ID NO:4:

(i) SEQUENCE CHARACTERISTICS:
             (A) LENGTH: 18 amino acids
             (B) TYPE: amino acid
             (D) TOPOLOGY: linear (ii) MOLECULE TYPE: peptide (v) FRAGMENT TYPE: internal (xi) SEQUENCE DESCRIPTION: SEQ ID NO:4:

Glu Arg Asn Ile Phe Asp Gln Arg Ala Ile Glu Asn Glu Leu Leu  Asp
1               5                  10                  15

Arg Lys (2) INFORMATION FOR SEQ ID NO:5:

(i) SEQUENCE CHARACTERISTICS:
             (A) LENGTH: 9 amino acids
             (B) TYPE: amino acid
             (D) TOPOLOGY: linear (ii) MOLECULE TYPE: peptide (v) FRAGMENT TYPE: internal (xi) SEQUENCE DESCRIPTION: SEQ ID NO:5:

Ala Ile Glu His Ala Asp Gly Gly Val
1               5

(2) INFORMATION FOR SEQ ID NO:6:

(i) SEQUENCE CHARACTERISTICS:
             (A) LENGTH: 474 amino acids
             (B) TYPE: amino acid
             (D) TOPOLOGY: linear (ii) MOLECULE TYPE: protein (xi) SEQUENCE DESCRIPTION: SEQ ID NO:6:

Met Ala Thr Ser Trp Gly Ser Ile Leu Gln Asp Glu Lys Gln Leu Glu
1               5                  10                  15

Glu Leu Ala Gln Gln Ala Ile Asp Arg Ala Leu Ala Glu Gly Val Leu
                20                  25                  30
```

```
Leu Arg Ser Ala Lys Asn Pro Ser Ser Asp Val Thr Tyr Ala
         35                  40                  45

Pro Phe Thr Leu Phe Pro Ser Pro Val Pro Ser Thr Leu Leu Glu Gln
 50                  55                  60

Ala Tyr Ala Val Gln Met Asp Phe Asn Ile Leu Val Asp Ala Val Ser
 65                  70                  75                  80

Gln Asn Ser Ala Phe Leu Glu Gln Thr Leu Ser Ser Thr Ile Lys Lys
                 85                  90                  95

Asp Glu Tyr Thr Ala Arg Leu Phe Asp Ile Tyr Lys Gln Val Leu Lys
                100                 105                 110

Glu Gly Ile Ala Gln Thr Val Phe Leu Gly Leu Asn Arg Ser Asp Tyr
                115                 120                 125

Met Phe Gln Cys Ser Ala Asp Gly Ser Lys Ala Leu Lys Gln Ile Glu
                130                 135                 140

Ile Asn Thr Ile Ser Ala Ser Phe Gly Gly Leu Ala Ser Arg Thr Pro
145                 150                 155                 160

Ala Val His Arg His Val Leu Asn Val Leu Asn Lys Thr Asn Glu Ala
                165                 170                 175

Ser Lys Ile Leu Ser Asn Asn Pro Ser Lys Gly Leu Ala Leu Gly Ile
                180                 185                 190

Ala Lys Ala Trp Glu Leu Tyr Gly Ser Ala Asn Ala Val Val Leu Leu
                195                 200                 205

Ile Ala Gln Glu Lys Glu Arg Asn Ile Phe Asp Gln Arg Ala Ile Glu
                210                 215                 220

Asn Glu Leu Leu Asp Arg Lys Ile His Val Ile Arg Arg Arg Phe Glu
225                 230                 235                 240

Asp Val Ser Glu Arg Gly Ser Leu Asp Gln Asn Arg Arg Leu Phe Met
                245                 250                 255

Glu Asp Gln Glu Val Ala Val Val Tyr Phe Arg Asp Gly Tyr Met Pro
                260                 265                 270

Ser Gln Tyr Asn Ala Gln Asn Trp Glu Ala Arg Leu Leu Leu Glu Arg
                275                 280                 285

Ser Cys Ala Ala Lys Cys Pro Asp Ile Ala Thr Gln Leu Ala Gly Thr
290                 295                 300

Lys Lys Val Gln Gln Glu Leu Ser Arg Val Gly Leu Leu Glu Ala Leu
305                 310                 315                 320

Leu Pro Gly Gln Pro Glu Ala Val Ala Arg Leu Arg Ala Thr Phe Ala
                325                 330                 335

Gly Leu Tyr Ser Leu Asp Met Gly Glu Glu Gly Asp Gln Ala Val Ala
                340                 345                 350

Glu Ala Leu Ala Ala Pro Ser His Phe Val Leu Lys Pro Gln Arg Glu
                355                 360                 365

Gly Gly Gly Asn Asn Phe Tyr Gly Glu Glu Met Val His Ala Leu Glu
                370                 375                 380

Gln Leu Lys Asp Ser Glu Glu Arg Ala Ser Tyr Ile Leu Met Glu Lys
385                 390                 395                 400

Ile Glu Pro Glu Pro Phe Arg Asn Cys Leu Leu Arg Pro Gly Ser Pro
                405                 410                 415

Ala Gln Val Val Gln Cys Ile Ser Glu Leu Gly Ile Phe Gly Val Tyr
                420                 425                 430

Val Arg Gln Gly Thr Thr Leu Val Met Asn Lys His Val Gly His Leu
                435                 440                 445
```

Leu Arg Thr Lys Ala Ile Glu His Ala Asp Gly Gly Val Ala Ala Gly
    450                 455                 460

Val Ala Val Leu Asp Asn Pro Tyr Pro Val
465                 470

(2) INFORMATION FOR SEQ ID NO:7:

(i) SEQUENCE CHARACTERISTICS:
        (A) LENGTH: 1905 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

```
TGGAGTTTGA GCTTGGCGAG CAGCTGGACA ACGAGCGAGT TGGGATGGCC ACCAGCTGGG      60
GAAGCATCTT GCAGGATGAG AAGCAGCTGG AAGAGTTGGC ACAGCAGGCC ATAGACCGGG     120
CCCTGGCTGA GGGGGTGTTG CTGAGGTCCG CAAAGAACCC CAGCTCCTCT GACGTGGTGA     180
CGTATGCCCC ATTCACGCTC TTCCCCTCAC CAGTGCCCAG CACTCTGCTG GAGCAGGCCT     240
ATGCTGTGCA GATGGACTTC AACATCCTGG TAGATGCTGT CAGCCAGAAC TCCGCCTTCC     300
TGGAGCAAAC ACTGTCTAGC ACCATCAAAA AGGATGAGTA TACTGCCCGT CTCTTTGATA     360
TCTACAAGCA AGTCCTGAAA GAGGGCATAG CCCAGACTGT GTTCCTGGGC CTCAATCGTT     420
CAGATTACAT GTTCCAGTGC AGCGCAGACG GCTCCAAAGC CCTGAAACAG ATTGAGATCA     480
ACACTATCTC TGCCAGCTTT GGGGGCCTGG CCTCCCGGAC TCCGGCTGTG CACCGACATG     540
TTCTCAATGT CCTGAATAAG ACCAACGAAG CTTCCAAGAT CCTGTCCAAC AACCCCAGCA     600
AGGGACTGGC CCTGGGGATC GCCAAAGCCT GGGAGCTCTA TGGCTCAGCC AATGCCGTGG     660
TGCTACTGAT TGCTCAGGAG AAGGAAAGGA ACATATTTGA CCAGCGTGCC ATAGAGAACG     720
AGCTGCTAGA CAGGAAGATC CATGTAATCC GCCGAAGATT TGAAGATGTC TCTGAAAGGG     780
GTTCTCTAGA CCAAAACCGA AGGCTGTTTA TGGAGGACCA GGAAGTTGCT GTGGTTTACT     840
TCCGAGATGG CTACATGCCC AGTCAGTATA ACGCACAGAA CTGGGAAGCT CGCCTGCTGC     900
TAGAGAGATC ATGTGCTGCC AAGTGTCCCG ACATTGCCAC ACAGCTGGCT GGCACTAAGA     960
AGGTGCAGCA GGAACTGAGC AGGGTGGGCC TGCTGGAAGC GCTGCTCCCG GGCCAGCCCG    1020
AGGCTGTGGC CCGCCTCCGT GCCACCTTTG CTGGCCTCTA TTCACTGGAC ATGGGTGAAG    1080
AAGGGGACCA GGCTGTCGCT GAGGCCCTTG CTGCCCCTAG CCACTTTGTG CTGAAGCCCC    1140
AAAGAGAGGG CGGAGGTAAT AACTTCTATG GGGAGGAAAT GGTACACGCT CTGGAGCAGC    1200
TGAAAGACAG CGAGGAGAGA GCCTCCTACA TCCTCATGGA GAAGATTGAA CCTGAGCCTT    1260
TTAGGAATTG CTTACTACGG CCTGGCAGCC CTGCCCAAGT GGTCCAGTGC ATCTCGGAGC    1320
TGGGTATTTT TGGAGTCTAT GTCAGACAGG GAACAACACT TGTGATGAAC AAGCATGTGG    1380
GGCATCTGCT TCGAACCAAA GCCATTGAAC ATGCAGATGG AGGTGTGGCA GCAGGAGTGG    1440
CAGTCCTGGA CAACCCCTAC CCTGTGTGAA GACATGTTCT GGGCTTCACT CAAGAGACCT    1500
TCTATCCTCT GTACTTGGCA CTCCTCTCCT GAGGGCTAC CCCTGTACCT GTGTTAGGGG    1560
AGGGAGCTTG TCTCTTTCAT AGACCTCCAG GGGCTTTAGG GAAGGGAAAA TCCCGGGTCC    1620
CTTCTCTCAG CCTTCCATCC AAGGACCAGA AAAGCTATGA TTCCATTGGA AGAGTTCTGG    1680
AGCTCCCCAG ATTTGGAGTG GGAATGGAAG CTCCTTTGAG GCAAAGGCCC ACAAACCCCA    1740
CACATCTTCA TTGCCCTCTC GCCAGCCTTT CCAGCAGGTT CTAGTGCCTT GACCTGGGGT    1800
```

-continued

```
AGGACCAAGT GACAGGAGGA AGAGGGTAGA TGGGCATAGA CTTCCCCAGC TCTGCCCTAA        1860

ATAAAACAAT GCTGATTCAA TGAAAAAAAA AAAAAAAAAA AAAAA                       1905

(2) INFORMATION FOR SEQ ID NO:8:

(i) SEQUENCE CHARACTERISTICS:
        (A) LENGTH: 1422 base pairs
        (B) TYPE: nucleic acid
        (C) STRANDEDNESS: single
        (D) TOPOLOGY: linear (ii) MOLECULE TYPE: DNA (genomic)

(v) FRAGMENT TYPE: internal (xi) SEQUENCE DESCRIPTION: SEQ ID NO:8:

ATGGCCACCA GCTGGGGAAG CATCTTGCAG GATGAGAAGC AGCTGGAAGA GTTGGCACAG          60

CAGGCCATAG ACCGGGCCCT GGCTGAGGGG GTGTTGCTGA GGTCCGCAAA GAACCCCAGC         120

TCCTCTGACG TGGTGACGTA TGCCCCATTC ACGCTCTTCC CCTCACCAGT GCCCAGCACT         180

CTGCTGGAGC AGGCCTATGC TGTGCAGATG GACTTCAACA TCCTGGTAGA TGCTGTCAGC         240

CAGAACTCCG CCTTCCTGGA GCAAACACTG TCTAGCACCA TCAAAAAGGA TGAGTATACT         300

GCCCGTCTCT TTGATATCTA CAAGCAAGTC CTGAAAGAGG GCATAGCCCA GACTGTGTTC         360

CTGGGCCTCA ATCGTTCAGA TTACATGTTC CAGTGCAGCG CAGACGGCTC CAAAGCCCTG         420

AAACAGATTG AGATCAACAC TATCTCTGCC AGCTTTGGGG GCCTGGCCTC CCGGACTCCG         480

GCTGTGCACC GACATGTTCT CAATGTCCTG AATAAGACCA ACGAAGCTTC CAAGATCCTG         540

TCCAACAACC CCAGCAAGGG ACTGGCCCTG GGGATCGCCA AAGCCTGGGA GCTCTATGGC         600

TCAGCCAATG CCGTGGTGCT ACTGATTGCT CAGGAGAAGG AAAGGAACAT ATTTGACCAG         660

CGTGCCATAG AGAACGAGCT GCTAGACAGG AAGATCCATG TAATCCGCCG AAGATTTGAA         720

GATGTCTCTG AAAGGGGTTC TCTAGACCAA AACCGAAGGC TGTTTATGGA GGACCAGGAA         780

GTTGCTGTGG TTTACTTCCG AGATGGCTAC ATGCCCAGTC AGTATAACGC ACAGAACTGG         840

GAAGCTCGCC TGCTGCTAGA GAGATCATGT GCTGCCAAGT GTCCCGACAT TGCCACACAG         900

CTGGCTGGCA CTAAGAAGGT GCAGCAGGAA CTGAGCAGGG TGGGCCTGCT GGAAGCGCTG         960

CTCCCGGGCC AGCCCGAGGC TGTGGCCCGC CTCCGTGCCA CCTTTGCTGG CCTCTATTCA        1020

CTGGACATGG GTGAAGAAGG GGACCAGGCT GTCGCTGAGG CCCTTGCTGC CCCTAGCCAC        1080

TTTGTGCTGA AGCCCCAAAG AGAGGGCGGA GGTAATAACT TCTATGGGGA GGAAATGGTA        1140

CACGCTCTGG AGCAGCTGAA AGACAGCGAG GAGAGAGCCT CCTACATCCT CATGGAGAAG        1200

ATTGAACCTG AGCCTTTTAG GAATTGCTTA CTACGGCCTG GCAGCCCTGC CCAAGTGGTC        1260

CAGTGCATCT CGGAGCTGGG TATTTTTGGA GTCTATGTCA GACAGGGAAC AACACTTGTG        1320

ATGAACAAGC ATGTGGGGCA TCTGCTTCGA ACCAAAGCCA TTGAACATGC AGATGGAGGT        1380

GTGGCAGCAG GAGTGGCAGT CCTGGACAAC CCCTACCCTG TG                          1422
```

RAT GLUTATHIONE SYNTHETASE GENE

This work was supported by National Institutes of Health Grant Nos. 2 R37 DK12034 (United States Public Health Service), and AI31804 (National Institute of Allergy and Infectious Diseases).

FIELD OF THE INVENTION

The present invention relates to a gene encoding mammalian glutathione synthetase, specifically rat glutathione synthetase, and the recombinant encoded protein.

BACKGROUND OF THE INVENTION

The tripeptide thiol glutathione (L-γ-glutamyl-L-cysteinylglycine; GSH) is found within virtually all cells. It functions in metabolism, transport, and cellular protection. Specifically, for example, glutathione participates in transhydrogenation reactions that are involved in the formation and maintenance of the sulfhydryl group of other molecules (e.g., coenzyme A, various enzymes, and other proteins). Glutathione provides reducing capacity for various reactions, e.g., the formation of deoxyribonucleotides by ribonucleotide reductase. Glutathione also functions in the detoxification of hydrogen peroxide, other peroxides, and free radicals. In addition, glutathione plays a role in detoxification of a variety of foreign compounds which interact with glutathione and which are ultimately excreted in the form of mercapturic acids. Analogous derivatives of glutathione are formed with endogenous metabolites, e.g., in the metabolism of leukotrienes, prostaglandins, steroids, and melanins. There is also evidence that the γ-glutamyl moiety of glutathione functions in the transport of amino acids (especially cysteine and certain neutral amino acids) and possibly also of peptides and amines.

Glutathione synthesis takes place within almost all animal cells and in those of many plants and microorganisms. The two enzymes required for the synthesis of this tripeptide (γ-glutamylcysteine synthetase and glutathione synthetase) have been isolated from a number of different sources (Dolphin, D., Poulson, R. and Avramovic, O. (eds.) (1989), *Glutathione: Chemical, Biochemical, and Medical Aspects*, Parts A and B, *Coenzyme and Cofactors Series*, Vol. III John Wiley, New York; Snoke, J. E. and Bloch, K. (1952), *J. Biol. Chem*. 199, 407–414; Snoke, J. E. (1955), *J. Biol. Chem*. 213, 813–842; Meister, A. (1974), in *The Enzymes* (Boyer, P. D., ed) 3rd Ed, Vol. 10, pp. 671–691, Academic Press, N.Y.).

Gamma-glutamylcysteine synthetase catalyzes the first and rate-limiting step of GSH synthesis (reaction (1)):

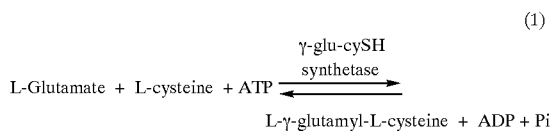

(1)

Gamma-glutamylcysteine is feedback inhibited by GSH. Richman, P., and Meister, A. (1975) *J. Biol. Chem*. 250, 1422–1426; Huang, C.-S., Chang, L.-S., Anderson, M. E., and Meister, A. (1993) *J. Biol. Chem*. 268, 19675–19678).

The amino acid sequences of the two separately coded proteins that comprise the two subunits of γ-glutamylcysteine synthetase in mammalian tissues have been deduced. Yan, N., and Meister, A. (1990), J. Biol. Chem. 265, 1588–1593; Huang, C.-S., Anderson, M. E., and Meister, A. (1993), *J. Biol. Chem*. 268, 20578–20583. This enzyme, which differs substantially in subunit structure and amino acid sequence from bacterial γ-glutamylcysteine synthetase, has been the subject of several studies. Yan, N., and Meister, A. (1990), *J. Biol. Chem*. 265, 1588–1593; Huang, C.-S., Anderson, M. E., and Meister, A. (1993), *J. Biol. Chem*. 268, 20578–20583; Huang, C.-S., Moore, W., and Meister, A. (1988), *Proc. Natl Acad. Sci.*, U.S.A. 85, 2464–2468; Seelig, G. F., and Meister, A. (1985), *Methods in Enzymology* 113, Chapter 47, pp. 379–390; Seelig, G. F., and Meister, A. (1984), *J. Biol. Chem*. 259, 3534–3538.

Glutathione synthetase, which catalyzes the synthesis of GSH from γ-glutamylcysteine and glycine, (reaction (2)):

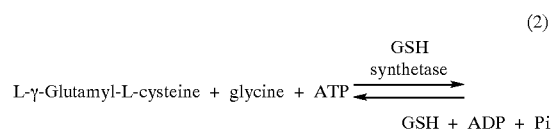

(2)

has also been purified from several biological sources. Meister, A. (1974), in *The Enzymes* (Boyer, P. D., ed) 3rd Ed, Vol. 10 pp. 671–691, Academic Press, N.Y. The GSH synthetase of *E. coli* was isolated as described in Gushima, H., Miya, T., Murata, K., and Kimura, A. (1983), *J. Appl. Biochem*. 5, 210–218 and Gushima, H., Yasuda, S., Soeda, E., Yokota, M., Kondo, M., and Kimura, A. (1984), *Nucl. Acids Res*. 12, 9299–9307. The purified *E. coli* enzyme, which had a $M_r$ 38,000, was cloned and sequenced. The enzymes purified from baker's yeast, described in Mooz, E. D. and Meister, A. (1967), *Biochemistry*, 6, 1722–1734, and fission yeast, described in Mutoh, N., Nakagawa, C. W., Ando, S., Tanabe, K., and Hayashi, Y. (1991), *Biochem. Biophys. Res. Comm*. 181, 430–436, each have a molecular weight of about 120,000. The fission yeast enzyme is reported to be a heterotetramer composed of two subunits with molecular weights of 33,000 and 26,000, respectively. See Mutoh, N., Nakagawa, C. W., Ando, S., Tanabe, K., and Hayashi, Y. (1991), *Biochem. Biophys. Res. Comm*. 181, 430–436. The DNA that codes for the heavy subunit was isolated and partially sequenced. When the heavy subunit DNA was introduced into the yeast, both the heavy subunit and the light subunit were overexpressed. The authors concluded that the enzyme is composed of 2 kinds of subunits and that it has an $A_2B_2$ structure. The gene for the large subunit of *Schizosaccharomyces pombe* was cloned from a *S. pombe* genomic DNA library by complementation of cadmium ion hypersensitivity of a GSH synthetase deficient *S. pombe* mutant, as described in Hayashi, Y., Nakagawa, C. W. and Mutoh, N. (1991), *Biochem. Cell Biol.*, 69, 115–121. Cadmium ions (and certain other metal ions) induce formation of phytochelatins, which have the general structure: (γ-glu-cys)$_n$-gly. See Grill, E., Loffler, S., Winnacker, E-L, and Zenk, M. H. (1989), *Proc. Natl. Acad. Sci. USA*, 86, 6838–6842; (cadystins, Hayashi, Y., Nakagawa, C. W. and Mutoh, N. (1991) *Biochem. Cell Biol.*, 69, 115–121). The mechanisms involved in the formation of these peptides are still under study, and the possibility that GSH synthetase activity is involved has been suggested. See Hayashi, Y., Nakagawa, C. W. and Mutoh, N. (1991) *Biochem. Cell Biol.*, 69, 115–121. Putative cDNA for frog GSH synthetase was isolated by using degenerative oligonucleotides derived arbitrarily from the deduced fission yeast amino acid sequence. Habenicht, A., Hille, S., and Knochel, W. (1993), *Biochem Biophys. Acta* 1174, 295–298. The proposed subunit structure of the frog enzyme needs to be substantiated since the enzyme has not yet been isolated.

However, expression of the enzyme using the putative frog cDNA has not been reported, and no activity for an enzyme encoded by the frog cDNA is known.

Rat kidney glutathione synthetase has also been isolated. Oppenheimer, L., Wellner, V., Griffith, O., and Meister, A. (1979), "Glutathione Synthetase Purification From Rat Kidney and Mapping of the Substrate Binding Sites," *J. Biol. Chem.*, 254, 5184–5190. However, the primary structure of the mammalian enzyme has not previously been described. Although, as noted above, some data on the amino acid sequences of the GSH synthetase of lower forms (e.g., bacteria, yeast) are available, there are major differences between certain properties of these enzymes and those of the rat kidney enzyme, for example, molecular weight, subunit structure, and inhibition by iodoacetamide.

Glutathione synthetase deficiency in humans is associated with potentially serious health complications. Two general types of such deficiency have been observed. Meister, A., and Larsson, A. (1994), "Glutathione Synthetase Deficiency and Other Disorders of the γ-Glutamyl Cycle," in *The Metabolic Basis of Inherited Disease*, (Scriver, C. R., Beaudet, A. L., Sly, W. S., and Valle, D. eds.) 7th Ed., in press. In one, an unstable form of GSH synthetase is expressed, leading to an apparently selective deficiency of GSH in the erythrocyte. In 5-oxoprolinuria, another type of GSH synthetase deficiency, dramatic and potentially fatal metabolic consequences occur as a result of over-production of 5-oxoproline which leads to severe metabolic acidosis. In this condition, there is over-production of γ-glutamylcysteine, whose synthesis is not feedback inhibited because of the low levels of GSH and possibly because there is induction of γ-glutamylcysteine synthetase. γ-Glutamylcysteine is converted by the action of γ-glutamylcyclotransferase to cysteine and 5-oxoproline. Cysteine is used by γ-glutamylcysteine synthetase (in a futile cycle), and 5-oxoproline accumulates in amounts that exceed the capacity of 5-oxoprolinase to convert it to glutamate. This leads to substantial accumulation of 5-oxoproline and to its urinary excretion in amounts that may be as high as 30 grams per day (normally <0.14 g. per day). Meister, A., and Larsson, A. (1994), "Glutathione Synthetase Deficiency and Other Disorders of the γ-Glutamyl Cycle," in *The Metabolic Basis of Inherited Disease*, (Scriver, C. R., Beaudet, A. L., Sly, W. S., and Valle, D. eds.) 7th Ed., in press. Severe damage to the central nervous system, and even potentially death, are among the potential complications.

Modifications of glutathione metabolism are sometimes desirable even in persons having normal glutathione levels. Such modifications may be achieved by administration of selective enzyme inhibitors to decrease intracellular glutathione levels, or by providing compounds that increase glutathione synthesis. Such effects are useful in chemotherapy and radiation therapy and in protecting cells against the toxic effects of drugs, other foreign compounds and oxygen.

Modification of GSH metabolism to deplete or increase cellular GSH may serve various purposes. For instance, it has long been known that thiols protect cells against the effects of irradiation. Since decreasing cellular GSH makes cells more susceptible to irradiation, glutathione depletion is useful in chemotherapeutic situations in which the cells to be killed and the cells to be spared have substantially different quantitative requirements for GSH. Depletion of GSH by inhibition of its synthesis also serves as a valuable adjuvant in chemotherapy with drugs that are detoxified by reactions involving GSH.

Conversely, development of resistance to a drug or to radiation may be associated with an increase in cellular GSH. GSH serves effectively in the detoxification of many drugs, and it is known that a significant pathway of acetaminophen detoxification involves conjugation with GSH.

Treatment with a thiazolidine such as L-2-oxothiazolidine-4-carboxylic acid, may be of value to patients with liver disease and to premature infants who may be deficient in the utilization of methionine sulfur for cysteine formation, and thus in GSH synthesis. The effectiveness of such a thiazolidine as an intracellular cysteine precursor depends on the presence of 5-oxoprolinase, an enzyme activity found in almost all animal cells.

Various methods are known to increase cellular levels of glutathione. Glutathione is composed of three amino acids: glutamic acid, cysteine and glycine. Administration to animals of the amino acid precursors of glutathione may produce an increase in cellular glutathione, but there is a limit to the effectiveness of this procedure. Concentrations of GSH are dependent on the supply of cysteine, which is derived from dietary protein and by trans-sulfuration from methionine in the liver. Administration of cysteine is not an ideal way to increase GSH concentration because cysteine is rapidly metabolized and furthermore, it is very toxic. Administration to animals of compounds that are transported into cells and converted intracellularly into cysteine is sometimes useful in increasing cellular glutathione levels. For example, the thiazolidine L-2-oxothiazolidine-4-carboxylate is transported into the cell, where it is converted by 5-oxoprolinase to L-cysteine, which is rapidly used for GSH synthesis.

Another way in which tissue GSH concentration may be increased is by administration of γ-glutamylcysteine or of γ-glutamylcysteine, as described in U.S. Pat. No. 4,879,370, which is hereby incorporated by reference. The administered γ-glutamyl amino acid is transported intact and serves as a substrate of GSH synthetase. It is also known that administration of N-acetyl-L-cysteine increases tissue concentrations of GSH, and although glutathione itself is not effectively transported into cells, half-esters and di-esters (ethyl, isopropyl, etc.) of glutathione are transported into, for example, liver and kidney cells, and so increase cellular glutathione levels, also as described in U.S. Pat. No. 4,879,370. However, complications limit the usefulness of these methods. For example, successful administration of N-acetyl-L-cysteine depends on the presence of de-acetylase (Greenstein, J. P. and Winitz, M. *Chemistry of the Amino Acid*, Wiley,N.Y. 1960, hereby incorporated by reference), and both γ-glutamylcysteine synthetase and glutathione synthetase, and ATP. Transporters for dipeptides, which apparently are not present in every cell, are required for treatment by administration of γ-glutamylcysteine or γ-glutamylcystine, which further requires glutathione synthetase and ATP. Glutathione esters are effective, but the effects are not long lasting, as the esters are metabolized relatively rapidly.

The present invention is directed toward overcoming these deficiencies.

SUMMARY OF THE INVENTION

The present invention relates to recombinant glutathione synthetase produced in an expression vector. The recombinant enzyme can be used to prepare glutathione analogs and radiolabelled glutathione.

The present invention also relates to an isolated DNA molecule encoding rat kidney glutathione synthetase. The molecule can be inserted as a heterologous (i.e. not naturally present) DNA in an expression system for producing the protein. Likewise, the heterologous DNA, usually inserted in the expression vector to form a recombinant DNA expression system, can be incorporated in a host cell to express the protein.

The DNA molecule of the present invention can be used in a method for increasing a cell's glutathione level. The DNA molecule is inserted in the cell in which an increase in glutathione is desired. The DNA molecule can also be used in a method for treating a mammal having a glutathione deficiency, wherein the DNA molecule is introduced into and expressed in the cells of the mammal to produce glutathione.

BRIEF DESCRIPTION OF THE DRAWINGS

FIG. 1 shows the amino acid sequences of the peptides obtained from isolated rat kidney GSH synthetase after trypsin cleavage (Peptides 1 (SEQ. ID. No. 1) and 2 (SEQ. ID. No. 2)) and after endopeptidase Lys C digestion (Peptides 3 to 5 (SEQ. ID. Nos. 3, 4, and 5, respectively)).

FIGS. 2A through 2D show the cDNA sequence (SEQ. ID. No. 7) coding for rat kidney GSH synthetase. The cDNA contains 1905 nucleotides. The open reading frame begins at nucleotide 45 and ends at nucleotide 1467 of the nucleotide sequence of SEQ. ID. No. 7 (corresponding to nucleotides 1 through 1423 shown in FIGS. 2A through 2C). The deduced amino acid sequence (SEQ. ID. No. 6) is shown under the cDNA sequence. The independently determined peptide sequences of FIG. 1 are underlined. A potential N-linked carbohydrate binding site is indicated by an asterisk (*). A possible O-linked carbohydrate binding site is indicated by (●).

DETAILED DESCRIPTION OF THE INVENTION

The present invention relates to isolated rat kidney glutatione. This protein has a calculated molecular weight of 52,344 daltons ($M_r$=52,344) and an amino acid sequence corresponding to SEQ. ID. No. 6 as follows:

```
Met Ala Thr Ser Trp Gly Ser Ile Leu Gln Asp Glu Lys Gln Leu Glu
1               5                   10                  15

Glu Leu Ala Gln Gln Ala Ile Asp Arg Ala Leu Ala Glu Gly Val Leu
            20                  25                  30

Leu Arg Ser Ala Lys Asn Pro Ser Ser Ser Asp Val Val Thr Tyr Ala
            35                  40                  45

Pro Phe Thr Leu Phe Pro Ser Pro Val Pro Ser Thr Leu Leu Glu Gln
        50                  55                  60

Ala Tyr Ala Val Gln Met Asp Phe Asn Ile Leu Val Asp Ala Val Ser
65                  70                  75                  80

Gln Asn Ser Ala Phe Leu Glu Gln Thr Leu Ser Ser Thr Ile Lys Lys
                85                  90                  95

Asp Glu Tyr Thr Ala Arg Leu Phe Asp Ile Tyr Lys Gln Val Leu Lys
                100                 105                 110

Glu Gly Ile Ala Gln Thr Val Phe Leu Gly Leu Asn Arg Ser Asp Tyr
            115                 120                 125

Met Phe Gln Cys Ser Ala Asp Gly Ser Lys Ala Leu Lys Gln Ile Glu
        130                 135                 140

Ile Asn Thr Ile Ser Ala Ser Phe Gly Gly Leu Ala Ser Arg Thr Pro
145                 150                 155                 160

Ala Val His Arg His Val Leu Asn Val Leu Asn Lys Thr Asn Glu Ala
            165                 170                 175

Ser Lys Ile Leu Ser Asn Asn Pro Ser Lys Gly Leu Ala Leu Gly Ile
                180                 185                 190

Ala Lys Ala Trp Glu Leu Tyr Gly Ser Ala Asn Ala Val Val Leu Leu
            195                 200                 205

Ile Ala Gln Glu Lys Glu Arg Asn Ile Phe Asp Gln Arg Ala Ile Glu
        210                 215                 220

Asn Glu Leu Leu Asp Arg Lys Ile His Val Ile Arg Arg Arg Phe Glu
225                 230                 235                 240

Asp Val Ser Glu Arg Gly Ser Leu Asp Gln Asn Arg Arg Leu Phe Met
                245                 250                 255

Glu Asp Gln Glu Val Ala Val Val Tyr Phe Arg Asp Gly Tyr Met Pro
                260                 265                 270

Ser Gln Tyr Asn Ala Gln Asn Trp Glu Ala Arg Leu Leu Leu Glu Arg
            275                 280                 285
```

```
Ser Cys Ala Ala Lys Cys Pro Asp Ile Ala Thr Gln Leu Ala Gly Thr
    290             295                 300

Lys Lys Val Gln Gln Glu Leu Ser Arg Val Gly Leu Leu Glu Ala Leu
305             310                 315                 320

Leu Pro Gly Gln Pro Glu Ala Val Ala Arg Leu Arg Ala Thr Phe Ala
                325                 330                 335

Gly Leu Tyr Ser Leu Asp Met Gly Glu Glu Gly Asp Gln Ala Val Ala
            340                 345                 350

Glu Ala Leu Ala Ala Pro Ser His Phe Val Leu Lys Pro Gln Arg Glu
            355                 360                 365

Gly Gly Gly Asn Asn Phe Tyr Gly Glu Glu Met Val His Ala Leu Glu
        370                 375                 380

Gln Leu Lys Asp Ser Glu Arg Ala Ser Tyr Ile Leu Met Glu Lys
385                 390                 395                 400

Ile Glu Pro Glu Pro Phe Arg Asn Cys Leu Leu Arg Pro Gly Ser Pro
                405                 410                 415

Ala Gln Val Val Gln Cys Ile Ser Glu Leu Gly Ile Phe Gly Val Tyr
                420                 425                 430

Val Arg Gln Gly Thr Thr Leu Val Met Asn Lys His Val Gly His Leu
        435                 440                 445

Leu Arg Thr Lys Ala Ile Glu His Ala Asp Gly Gly Val Ala Ala Gly
    450                 455                 460

Val Ala Val Leu Asp Asn Pro Tyr Pro Val
465                 470
```

Another aspect of the present invention relates to a DNA molecule encoding the protein of the present invention. As to the rat glutathione protein, the DNA molecule comprises a nucleotide sequence corresponding to SEQ. ID. No. 7 as follows:

```
TGGAGTTTGA GCTTGGCGAG CAGCTGGACA ACGAGCGAGT TGGGATGGCC ACCAGCTGGG    60
GAAGCATCTT GCAGGATGAG AAGCAGCTGG AAGAGTTGGC ACAGCAGGCC ATAGACCGGG   120
CCCTGGCTGA GGGGGTGTTG CTGAGGTCCG CAAAGAACCC CAGCTCCTCT GACGTGGTGA   180
CGTATGCCCC ATTCACGCTC TTCCCCTCAC CAGTGCCCAG CACTCTGCTG GAGCAGGCCT   240
ATGCTGTGCA GATGGACTTC AACATCCTGG TAGATGCTGT CAGCCAGAAC TCCGCCTTCC   300
TGGAGCAAAC ACTGTCTAGC ACCATCAAAA AGGATGAGTA TACTGCCCGT CTCTTTGATA   360
TCTACAAGCA AGTCCTGAAA GAGGGCATAG CCCAGACTGT GTTCCTGGGC CTCAATCGTT   420
CAGATTACAT GTTCCAGTGC AGCGCAGACG GCTCCAAAGC CCTGAAACAG ATTGAGATCA   480
ACACTATCTC TGCCAGCTTT GGGGGCCTGG CCTCCCGGAC TCCGGCTGTG CACCGACATG   540
TTCTCAATGT CCTGAATAAG ACCAACGAAG CTTCCAAGAT CCTGTCCAAC AACCCCAGCA   600
AGGGACTGGC CCTGGGGATC GCCAAAGCCT GGGAGCTCTA TGGCTCAGCC AATGCCGTGG   660
TGCTACTGAT TGCTCAGGAG AAGGAAAGGA ACATATTTGA CCAGCGTGCC ATAGAGAACG   720
AGCTGCTAGA CAGGAAGATC CATGTAATCC GCCGAAGATT TGAAGATGTC TCTGAAAGGG   780
GTTCTCTAGA CCAAAACCGA AGGCTGTTTA TGGAGGACCA GGAAGTTGCT GTGGTTTACT   840
TCCGAGATGG CTACATGCCC AGTCAGTATA ACGCACAGAA CTGGGAAGCT CGCCTGCTGC   900
TAGAGAGATC ATGTGCTGCC AAGTGTCCCG ACATTGCCAC ACAGCTGGCT GGCACTAAGA   960
AGGTGCAGCA GGAACTGAGC AGGGTGGGCC TGCTGGAAGC GCTGCTCCCG GGCCAGCCCG  1020
AGGCTGTGGC CCGCCTCCGT GCCACCTTTG CTGGCCTCTA TTCACTGGAC ATGGGTGAAG  1080
```

-continued

```
AAGGGGACCA GGCTGTCGCT GAGGCCCTTG CTGCCCCTAG CCACTTTGTG CTGAAGCCCC   1140
AAAGAGAGGG CGGAGGTAAT AACTTCTATG GGGAGGAAAT GGTACACGCT CTGGAGCAGC   1200
TGAAAGACAG CGAGGAGAGA GCCTCCTACA TCCTCATGGA GAAGATTGAA CCTGAGCCTT   1260
TTAGGAATTG CTTACTACGG CCTGGCAGCC CTGCCCAAGT GGTCCAGTGC ATCTCGGAGC   1320
TGGGTATTTT TGGAGTCTAT GTCAGACAGG GAACAACACT TGTGATGAAC AAGCATGTGG   1380
GGCATCTGCT TCGAACCAAA GCCATTGAAC ATGCAGATGG AGGTGTGGCA GCAGGAGTGG   1440
CAGTCCTGGA CAACCCCTAC CCTGTGTGAA GACATGTTCT GGGCTTCACT CAAGAGACCT   1500
TCTATCCTCT GTACTTGGCA CTCCTCTCCT GAGGGGCTAC CCCTGTACCT GTGTTAGGGG   1560
AGGGAGCTTG TCTCTTTCAT AGACCTCCAG GGGCTTTAGG GAAGGGAAAA TCCCGGGTCC   1620
CTTCTCTCAG CCTTCCATCC AAGGACCAGA AAAGCTATGA TTCCATTGGA AGAGTTCTGG   1680
AGCTCCCCAG ATTTGGAGTG GGAATGGAAG CTCCTTTGAG GCAAAGGCCC ACAAACCCCA   1740
CACATCTTCA TTGCCCTCTC GCCAGCCTTT CCAGCAGGTT CTAGTGCCTT GACCTGGGGT   1800
AGGACCAAGT GACAGGAGGA AGAGGGTAGA TGGGCATAGA CTTCCCCAGC TCTGCCCTAA   1860
ATAAAACAAT GCTGATTCAA TGAAAAAAAA AAAAAAAAA AAAAA                    1905
```

Yet another aspect of the invention relates to a DNA molecule encoding the protein of the present invention. The DNA molecule comprises a nucleotide sequence corresponding to SEQ. ID. No. 8 as follows:

```
ATGGCCACCA GCTGGGGAAG CATCTTGCAG GATGAGAAGC AGCTGGAAGA GTTGGCACAG     60
CAGGCCATAG ACCGGGCCCT GGCTGAGGGG GTGTTGCTGA GGTCCGCAAA GAACCCCAGC    120
TCCTCTGACG TGGTGACGTA TGCCCCATTC ACGCTCTTCC CCTCACCAGT GCCCAGCACT    180
CTGCTGGAGC AGGCCTATGC TGTGCAGATG GACTTCAACA TCCTGGTAGA TGCTGTCAGC    240
CAGAACTCCG CCTTCCTGGA GCAAACACTG TCTAGCACCA TCAAAAAGGA TGAGTATACT    300
GCCCGTCTCT TTGATATCTA CAAGCAAGTC CTGAAAGAGG GCATAGCCCA GACTGTGTTC    360
CTGGGCCTCA ATCGTTCAGA TTACATGTTC CAGTGCAGCG CAGACGGCTC CAAAGCCCTG    420
AAACAGATTG AGATCAACAC TATCTCTGCC AGCTTTGGGG GCCTGGCCTC CCGGACTCCG    480
GCTGTGCACC GACATGTTCT CAATGTCCTG AATAAGACCA ACGAAGCTTC CAAGATCCTG    540
TCCAACAACC CCAGCAAGGG ACTGGCCCTG GGGATCGCCA AAGCCTGGGA GCTCTATGGC    600
TCAGCCAATG CCGTGGTGCT ACTGATTGCT CAGGAGAAGG AAAGGAACAT ATTTGACCAG    660
CGTGCCATAG AGAACGAGCT GCTAGACAGG AAGATCCATG TAATCCGCCG AAGATTTGAA    720
GATGTCTCTG AAAGGGGTTC TCTAGACCAA AACCGAAGGC TGTTTATGGA GGACCAGGAA    780
GTTGCTGTGG TTTACTTCCG AGATGGCTAC ATGCCCAGTC AGTATAACGC ACAGAACTGG    840
GAAGCTCGCC TGCTGCTAGA GAGATCATGT GCTGCCAAGT GTCCCGACAT TGCCACACAG    900
CTGGCTGGCA CTAAGAAGGT GCAGCAGGAA CTGAGCAGGG TGGGCCTGCT GGAAGCGCTG    960
CTCCCGGGCC AGCCCGAGGC TGTGGCCCGC CTCCGTGCCA CCTTTGCTGG CCTCTATTCA   1020
CTGGACATGG GTGAAGAAGG GGACCAGGCT GTCGCTGAGG CCCTTGCTGC CCCTAGCCAC   1080
TTTGTGCTGA AGCCCAAAG AGAGGGCGGA GGTAATAACT TCTATGGGGA GGAAATGGTA    1140
CACGCTCTGG AGCAGCTGAA AGACAGCGAG GAGAGAGCCT CCTACATCCT CATGGAGAAG   1200
ATTGAACCTG AGCCTTTTAG GAATTGCTTA CTACGGCCTG GCAGCCCTGC CCAAGTGGTC   1260
```

```
                                             -continued
CAGTGCATCT CGGAGCTGGG TATTTTTGGA GTCTATGTCA GACAGGGAAC AACACTTGTG  1320

ATGAACAAGC ATGTGGGGCA TCTGCTTCGA ACCAAAGCCA TTGAACATGC AGATGGAGGT  1380

GTGGCAGCAG GAGTGGCAGT CCTGGACAAC CCCTACCCTG TG                    1422
```

The protein of the present invention is preferably produced in purified form by conventional techniques. Typically, rat kidneys are homogenized and centrifuged. The supernatant is then subjected to sequential ammonium sulfate precipitation and heat treatment. The fraction containing the protein of the present invention is subjected to gel filtration in an appropriately sized dextran or polyacrylamide column to separate the proteins. If necessary, the protein fraction may be further purified by HPLC.

The DNA molecule of the present invention can be incorporated in cells using conventional recombinant DNA technology. The DNA molecule may be inserted into an expression system to which the DNA molecule is heterologous (i.e. not normally present). Alternatively, as described more fully below, the DNA molecule may be introduced into cells which normally contain the DNA molecule, as, for example, to correct a deficiency or defect in glutathione synthetase expression, or where over-expression of the enzyme is desired.

For expression in heterologous systems, the heterologous DNA molecule is inserted into the expression system or vector in proper sense orientation and correct reading frame. The vector contains the necessary elements for the transcription and translation of the inserted protein-coding sequences.

U.S. Pat. No. 4,237,224 to Cohen and Boyer, which is hereby incorporated by reference, describes the production of expression systems in the form of recombinant plasmids using restriction enzyme cleavage and ligation with DNA ligase. These recombinant plasmids are then introduced by means of transformation and replicated in unicellular cultures including procaryotic organisms and eucaryotic cells grown in tissue culture.

Recombinant genes may also be introduced into viruses, such as vaccinia virus. Recombinant viruses can be generated by transfection of plasmids into cells infected with virus.

Suitable vectors include, but are not limited to, the following viral vectors such as lambda vector system gt11, gt WES.tB, Charon 4, and plasmid vectors such as pBR322, pBR325, pACYC177, pACYC184, pUC8, pUC9, pUC18, pUC19, pLG339, pR290, pKC37, pKC101, SV 40, pBluescript II SK +/− or KS +/− (see "Stratagene Cloning Systems" Catalog (1993) from Stratagene, La Jolla, Calif., which is hereby incorporated by reference), pQE, pIH821, PGEX, pET series (see F. W. Studier et. al. (1990), "Use of T7 RNA Polymerase to Direct Expression of Cloned Genes," *Gene Expression Technology* vol. 185, which is hereby incorporated by reference) and any derivatives thereof. Recombinant molecules can be introduced into cells via transformation, particularly transduction, conjugation, mobilization, or electroportation. The DNA sequences are cloned into the vector using standard cloning procedures in the art, as described by Maniatis et al., *Molecular Cloning: A Laboratory Manual*, Cold Springs Laboratory, Cold Springs Harbor, N.Y. (1982), which is hereby incorporated by reference.

A variety of host-vector systems may be utilized to express the protein-encoding sequence(s). Primarily, the vector system must be compatible with the host cell used. Host-vector systems include but are not limited to the following: bacteria transformed with bacteriophage DNA, plasmid DNA, or cosmid DNA; microorganisms such as yeast containing yeast vectors; mammalian cell systems infected with virus (e.g., vaccinia virus, adenovirus, etc.); insect cell systems infected with virus (e.g., baculovirus). The expression elements of these vectors vary in their strength and specificities. Depending upon the host-vector system utilized, any one of a number of suitable transcription and translation elements can be used.

Different genetic signals and processing events control many levels of gene expression (e.g., DNA transcription and messenger RNA (mRNA) translation).

Transcription of DNA is dependent upon the presence of a promoter which is a DNA sequence that directs the binding of RNA polymerase and thereby promotes mRNA synthesis. The DNA sequences of eucaryotic promoters differ from those of procaryotic promoters. Furthermore, eucaryotic promoters and accompanying genetic signals may not be recognized in or may not function in a procaryotic system, and, further, procaryotic promoters are not recognized and do not function in eucaryotic cells.

Similarly, translation of mRNA in procaryotes depends upon the presence of the proper procaryotic signals which differ from those of eucaryotes. Efficient translation of mRNA in procaryotes requires a ribosome binding site called the Shine-Dalgarno (SD) sequence on the mRNA. This sequence is a short nucleotide sequence of mRNA that is located before the start codon, usually AUG, which encodes the amino-terminal methionine of the protein. The SD sequences are complementary to the 3'-end of the 16S rRNA (ribosomal RNA) and probably promote binding of mRNA to ribosomes by duplexing with the rRNA to allow correct positioning of the ribosome. For a review on maximizing gene expression, see Roberts and Lauer, *Methods in Enzymology*, 68:473 (1979), which is hereby incorporated by reference.

Promoters vary in their "strength" (i.e. their ability to promote transcription). For the purposes of expressing a cloned gene, it is desirable to use strong promoters in order to obtain a high level of transcription and, hence, expression of the gene. Depending upon the host cell system utilized, any one of a number of suitable promoters may be used. For instance, when cloning in *E. coli*, its bacteriophages, or plasmids, promoters such as the T7 phage promoter, lac promotor, trp promotor, recA promotor, ribosomal RNA promotor, the $P_R$ and $P_L$ promoters of coliphage lambda and others, including but not limited, to lacUV5, ompF, bla, lpp, and the like, may be used to direct high levels of transcription of adjacent DNA segments. Additionally, a hybrid trp-lacUV5 (tac) promotor or other *E. coli* promoters produced by recombinant DNA or other synthetic DNA techniques may be used to provide for transcription of the inserted gene.

Bacterial host cell strains and expression vectors may be chosen which inhibit the action of the promotor unless specifically induced. In certain operons, the addition of specific inducers is necessary for efficient transcription of the inserted DNA. For example, the lac operon is induced by the addition of lactose or IPTG (isopropylthio-beta-D-galactoside). A variety of other operons, such as trp, pro, etc., are under different controls.

Specific initiation signals are also required for efficient gene transcription and translation in procaryotic cells. These transcription and translation initiation signals may vary in "strength" as measured by the quantity of gene specific messenger RNA and protein synthesized, respectively. The DNA expression vector, which contains a promoter, may also contain any combination of various "strong" transcription and/or translation initiation signals. For instance, efficient translation in *E. coli* requires a Shine-Dalgarno (SD) sequence about 7–9 bases 5' to the initiation codon (ATG) to provide a ribosome binding site. Thus, any SD-ATG combination that can be utilized by host cell ribosomes may be employed. Such combinations include but are not limited to the SD-ATG combination from the cro gene or the N gene of coliphage lambda, or from the *E. coli* tryptophan E, D, C, B or A genes. Additionally, any SD-ATG combination produced by recombinant DNA or other techniques involving incorporation of synthetic nucleotides may be used.

Once the isolated DNA molecule of the present invention has been cloned into an expression system, it is ready to be incorporated into a host cell. Such incorporation can be carried out by the various forms of transformation noted above, depending upon the vector/host cell system. Suitable host cells include, but are not limited to, bacteria, virus, yeast, mammalian cells, and the like.

In view of the present invention's discovery of recombinant rat glutathione synthetase, a wide array of therapeutic and/or prophylactic agents and diagnostic procedures for, respectively, treating and detecting glutathione synthetase deficiency can be developed. The recombinant enzyme can be used to make glutathione, analogs of glutathione, and radiolabelled glutathione from various amino acid starting materials. For example, radiolabelled L-γ-glutamyl-L-cysteine prepared from L-glutamate labelled, for example, with $C^{14}$, tritium or other radiolabel, or from cysteine labelled with $S^{35}$, $C^{14}$, or tritium, can be converted to radiolabelled glutathione using the recombinant enzyme of the invention. In addition, the recombinant enzyme is not strictly selective, and can, therefore, be used to prepare radioactive or non-radioactive analogs of glutathione from other γ-glutamyl amino acids (for example, γ-glutamyl-β-alanine), analogs of both cysteine (such as β-alanine) and glycine, and other amino acids. An example of such a glutathione analog is ophthalmic acid, prepared from γ-glutamyl-α-amino butyrate. Examples of other suitable γ-glutamyl amino acids are listed in U.S. Pat. No. 4,758,551, which is hereby incorporated by reference.

The recombinant enzyme of the invention can also be used in enzyme assays, and to raise antibodies useful, for example, in ELISA and radioimmune assays.

In a diagnostic embodiment of the present invention, the nucleotide sequence of the isolated DNA molecule of the present invention may be used as a probe in nucleic acid hybridization assays for the detection of the glutathione synthetase gene in various patient body fluids. The nucleotide sequence of the present invention may be used in any nucleic acid hybridization assay system known in the art, including, but not limited to, Southern blots (Southern, *J. Mol. Biol.*, 98:508 (1975); Northern blots (Thomas et al., *Proc. Nat'l Acad. Sci. USA*, 77:5201–05 (1980)); Colony blots (Grunstein et al., *Proc. Nat'l Acad. Sci. USA*, 72:3961–65 (1975), which are hereby incorporated by reference). Alternatively, the isolated DNA molecule of the present invention can be used in a gene amplification detection procedure such as a polymerase chain reaction (H. A. Erlich et al., "Recent Advances in the Polymerase Chain Reaction", *Science* 252:1643–51 (1991), which is hereby incorporated by reference) or in restriction fragment length polymorphism (RFLP) diagnostic techniques, as described in J. D. Watson et al., Recombinant DNA, Scientific American Books, pp. 519–522, 545–547 (2d ed. 1992), which is hereby incorporated by reference.

Specifically, for example, the DNA molecules of the invention can be used in prenatal diagnosis of the human diseases associated with defects in GSH synthetase. A probe for the DNA encoding the synthetase enzyme can be designed using the DNA molecule of the invention, and used to probe the DNA obtained from amniotic fluid or chorionic tissue and amplified by PCR for the presence of the synthetase gene, as noted above. Similar procedures can be used in postnatal diagnostic work, as, for example, to diagnose the source of a glutathione deficiency in a person who is acidotic.

Another potentially useful application of the DNA molecule of the present invention is the possibility of increasing the amount of enzyme present in a mammal by gene transfer (so-called "gene therapy"). A model for this type of gene transfer and for its potential usefulness has been found in connection with studies on a strain of *E. coli* whose radioresistance was enhanced by enrichment of its content of the enzyme required for glutathione synthesis by recombinant DNA techniques. *Proc. Natl. Acad. Sci, U.S.* 86:1461 (1989). Gene transfer of the gene of the present invention would also be expected to give a similar result, and it would also be expected that the biochemical reactions associated with glutathione would also be enhanced by such a genetic transfer of this gene into an animal host. Of course, in most instances, this gene would be transferred into the animal host along with promoters, inducers, and the like (which are well known and recognized techniques in the field of genetic engineering, as noted supra) to allow the cell to initiate and continue production of the genetic product protein. The DNA molecule of the present invention can be transferred into the extra-chromosomal or genomic DNA of the host.

Another potential application for the present DNA molecule is to introduce antisense oligonucleotide sequences to a cell as a means to inhibit GSH production by the cell. 5-oxoprolinuria may result, but this condition may be desirable where, for example, glutathione depletion is useful in chemotherapy and radiation therapy.

Probes prepared using the DNA molecule of the invention, or certain fragments thereof, may also be used to assay and measure the concentration of mRNA for the enzyme in clinical specimens obtained from animal sources.

The DNA molecule of the present invention can also be used to construct models for evaluation of potential therapies for a variety of conditions. For example, as discussed above, glutathione protects cells from damage from certain chemotherapies and excesses of other drugs such as particular painkillers, as well as from the effects of radiation. Cell lines constructed using the DNA molecule of the invention can be used to evaluate the potential effects of these agents on various types of animal cells.

EXAMPLES

Example 1

GSH Synthetase Activity

Glutathione synthetase enzymatic activity was determined spectrophotometrically by following the formation of ADP using a coupled assay containing pyruvate kinase and lactate dehydrogenase. Seelig, G. F., and Meister, A. (1985), *Methods in Enzymology* v. 113, chpt. 47, pp. 379–390, hereby incorporated by reference. The reaction mixture (1 ml) contained Tris-HCl buffer (100 mM; pH 8.2), γ-L-glutamyl-L-α-aminobutyrate (2 mM), glycine (10 mM), magnesium chloride (20 mM), disodium ATP (5 mM), sodium phosphoenolpyruvate (2 mM), potassium chloride (150 mM), NADH (2 mM), pyruvate kinase (5 units), and lactate dehydrogenase (10 units). The reaction was initiated by addition of the enzyme sample. The rate of decrease in the absorbance at 340 nm was followed at 37° C. A unit of enzyme activity is defined as the amount that catalyzes the formation of 1 μmole of product per hour.

Example 2
Purification of GSH Synthetase

GSH synthetase was isolated from rat kidney by ammonium sulfate fractionation, heat treatment, DE52 and Sephadex G-150 column chromatography as described by Oppenheimer, L., Wellner, V. P., Griffith, O. W., and Meister, A. (1979), *J. Biol. Chem.* 254, 5184–5190, hereby incorporated by reference. The enzyme was further processed by chromatography on a Phenyl-5PW HPLC column (Bio-Rad) equilibrated with 50 mM imidazole-HCl buffer (pH 7.4) containing 1 mM EDTA and 0.5 M ammonium sulfate (starting buffer). The column was eluted with a linear gradient established between the starting buffer and an imidazole-HCl buffer (50 mM; pH 7.4) containing 1 mM EDTA for 40 min. Fractions of 1 ml were collected. The fractions containing enzyme activity were pooled and dialyzed against 50 MM imidazole-HCl buffer (pH 7.4): The specific activity was 780 units/mg. SDS-polyacrylamide gel electrophoresis analysis showed apparent homogeneity (>99%) and a molecular weight of 55,000.

Example 3
Preparation of Antibody Against Rat Kidney GSH Synthetase

The synthetase (0.1 mg dissolved in 1 ml of PBS buffer) was mixed vigorously with 1 ml of complete Freund's adjuvant until the solution became very viscous. Anesthetized New Zealand white rabbits (4 lbs) were injected intradermally with 10 portions (0.2 ml each) of the emulsion. The animals were given a second dose of a mixture containing the protein (0.1 mg) mixed with the same volume of incomplete Freund's adjuvant six weeks later. The titer of the antiserum was monitored with ELISA. Since the antibody obtained apparently reacts with *E. coli* protein, the antiserum was pre-absorbed with the *E. coli* protein by incubating it with nitrocellulose that had been saturated with *E. coli* total protein before immunoscreening.

Example 4
Peptide Sequence Analysis

The protein was digested with trypsin and with Endopeptidase Lys C as described in Matsudaira, P. (1987), *J. Biol. Chem.* 262, 10035–10038, Aebersold, R. H., Leavitt, J., Saavedra, R. A., Hood, L. E., and Kent, S. B. H. (1987), *Proc. Natl. Acad. Sci. U.S.A.* 84, 6970–6974, each of which is hereby incorporated by reference. Rat kidney GSH synthetase (1 mg) was subjected to SDS polyacrylamide electrophoresis and electrotransferred to a polyvinylidene difluoride (PVDF) membrane. The membrane was stained with Amido Black and the protein band with molecular weight of 55,000 was cut off the membrane and blotted with 0.5% polyvinylpyrrolidone 40 (PVP-40). The membrane was then treated with trypsin (10% w/w) and Endopeptidase Lys-C (10% w/w) in Tris-HCl buffer (0.1 M; pH 8.2) containing 5% acetonitrile. The peptides obtained were separated on HPLC by use of a μBondapack C18 reversed phase column (Waters) developed with a 0 to 80% acetonitrile gradient in 0.1% trifluoroacetic acid. Peptide sequencing was carried out at the Rockefeller University Peptide Sequencing Facility.

Example 5
Isolation of the cDNA Clone for GSH Synthetase

A rat kidney cDNA λgt11 expression library (Clontech) was immunoscreened as described in Sambrook, J., Fritsh, E. F., and Maniatis, T. (1989), *Molecular Cloning: A Laboratory Manual*, 2nd Ed., Cold Spring Harbor Laboratory, Cold Spring Harbor, N.Y., which is hereby incorporated by reference, using the antiserum against rat kidney GSH synthetase pre-absorbed with *E. coli* total protein. An overnight culture of *E. coli* Y1090r⁻ was incubated with $10^6$ plaque-forming units (pfu) of bacteriophage λgt11 at 37° C. for 15 min. A suspension of the infected bacteria was poured on to 20 LB agar plates (150×35 mm) and incubated at 42° C. for 3 h. The plates were covered with IPTG-treated nitrocellulose membranes and incubated at 37° C. for an additional 4 h. The filters were carefully peeled off the plates and rinsed with TNT buffer (10 mM Tris-HCl (pH 8.0), 150 mM NaCl, and 0.05% Tween 20). The plates were covered with a second set of nitrocellulose filters and incubated at 37° C. for 6 h.

The two sets of nitrocellulose filters were treated with blocking buffer (TNT buffer containing 5% nonfat dry milk) for 1 h. The filters were treated with TNT buffer containing diluted (1:200) antibody to rat kidney GSH synthetase for an additional 4 h. After washing thrice with TNT buffer, the filters were then incubated with diluted peroxidase-linked goat anti-rabbit IgG antibody (1:5000) for 1 h. After washing 5 times, the antibody was visualized by treating the filters with Tris-HCl buffer (50 mM; pH 7.5) containing 0.018% $H_2O_2$ and 0.06% 3,3'-diaminobenzidine for 5 min. The plaques that appeared positive on both sets of the filters were picked, grown, and re-screened with the same antibody. The positive clone was confirmed by Western blot analysis using the total protein obtained from the *E. coli* infected with the phage in the positive plaque.

Example 6
Purification of Recombinant λDNA

The purification was performed as described in Ausubel, F. M., Brent, R., Kingston, R. E., Moore, D. D., Seidman, J. G., Smith, J. A., and Struhl, K. (1988), *Current Protocols in Molecular Biology*, Greene Publishing Associates/Wiley-Interscience, New York, hereby incorporated by reference. Recombinant λ phage particles (1×$10^6$ pfu) obtained from the positive clone was incubated with *E. coli* Y1090r⁻ (1×$10^8$ cells) at 37° C. for 20 min. The infected cells were inoculated into 100 ml of NZCYM medium until the cells lysed. After removal of cellular debris by centrifugation (8,000×g, 5 min), the λ phage was sedimented (25,000 rpm, SW28 rotor, 2 h). An aqueous solution of the phage was then treated with phenol, saturated with tris buffer (pH 8), and then the aqueous layer was treated with phenol/chloroform (1:1); the remaining aqueous layer was processed as described in Sambrook, J., Fritsh, E. F., and Maniatis, T. (1989), *Molecular Cloning: A Laboratory Manual*, 2nd Ed., Cold Spring Harbor Laboratory, Cold Spring Harbor, N.Y., which is hereby incorporated by reference, to obtain the DNA. The DNA was precipitated by adding ethanol and dissolved in 50 μl of Tris-HCl (10 mM; pH 7.6) buffer containing 1 mM EDTA.

Example 7

DNA Sequence Analysis

The insert cDNA in the λDNA was excised by treatment with restriction enzyme BsiW1 and isolated by agarose gel electrophoresis. The cDNA was then blunt-ended with *E. Coli* DNA polymerase I Klenow fragment and subcloned into the Sma I site of pBluescript KS(+). The nucleotide sequence was determined by the dideoxynucleotide chain termination method described in Sanger, F., Nicklen, S., and Coulson, A. R. (1977), *Proc. Natl. Acad. Sci. U.S.A.* 74, 5463–5467, which is hereby incorporated by reference, using Sequenase (U.S. Biochemical Corp.) following the manufacturer's instructions. Sequence analysis was carried out using the PC/Gene Software at the Rockefeller University Computer Service.

Example 8

Northern Blot Analysis

A charged nylon membrane containing mRNA (2 μg each) from various rat tissues (Clontech) was used. The membrane was incubated with the prehybridization buffer (5×SSPE containing 10× Denhardt's solution, 50% formamide, 2% SDS, and 100 μg denatured salmon sperm DNA) as described in Sambrook, J., Fritsh, E. F., and Maniatis, T. (1989), *Molecular Cloning: A Laboratory Manual*, 2nd Ed., Cold Spring Harbor Laboratory, Cold Spring Harbor, N.Y., at 42° C. for 18 h with the Sma I fragment (682 bp) of the synthetase cDNA labeled with $^{32}$P by nick translation (~2× $10^8$ cpm/μg). The membrane was washed twice with 2×SSPE containing 0.05% SDS at room temperature and twice for 40 min each in 0.1×SSPE containing 0.1% SDS at 50° C. Autoradiography was performed at −70° C. for 4 days.

Example 9

Characterization of the Peptides Obtained from Rat Kidney GSH Synthetase

Tryptic peptides of rat kidney GSH synthetase were separated on a C18 reversed phase column. Two apparently homogeneous peptides were obtained and their sequences were determined by the automated Edman degradation method (peptides 1 and 2, FIG. 1). To obtain larger peptides, the protein was treated with Endopeptidase Lys-C. Three peptides were obtained and sequenced (peptides 3–5, FIG. 1).

Example 10

Isolation of the cDNA Clone Coding for Rat Kidney GSH Synthetase

A rat kidney cDNA λgt11 expression library, which contains cDNA inserts in the phage EcoRI site, was screened with the antibody against rat kidney GSH synthetase. One clone was obtained from about $10^6$ phages. The clone was confirmed to be positive by the finding that the expressed fusion protein reacted with the antibody as determined by Western blot analysis (data not shown). An attempt to excise the cDNA insert by treating the λDNA with EcoRI failed indicating that the site was lost during the construction of the cDNA library. The DNA was subsequently treated with BsiWI, which cut the λDNA at sites that were about 200 bp away from the ends of the cDNA insert, and the insert DNA of 2.3 kb was separated by agarose gel electrophoresis. The cDNA was blunt-ended and subcloned into the SmaI site of pBluescript KS-(+) for sequence analysis.

Example 11

Nucleotide Sequence of the cDNA for Rat Kidney GSH Synthetase

The cDNA sequence corresponding to rat kidney GSH synthetase mRNA is presented in FIG. 2. The entire positive strand was sequenced at least twice from different overlapping sets using internal primers. The sequence was confirmed completely by sequencing the complementary strand. The sequence contains 1905 nucleotides and an open reading frame of 1422 nucleotides that codes for 474 amino acid residues. The cDNA also has a 3'-nontranslated region of 439 nucleotides including a poly A tail. The first ATG at position 1 in FIG. 2 (nucleotide 45 in the nucleotide sequence of SEQ. ID. No. 7) is thought to be the translation start codon. The open reading frame starting with this ATG codon encodes a protein of molecular weight 52,344, which is in close agreement with the molecular weight value 55,000 estimated by SDS gel electrophoresis of the purified rat kidney enzyme. The open reading frame sequence ends with the termination codon TGA at position 1423 shown in FIG. 2 (nucleotide 1467 in the nucleotide sequence of SEQ. ID. No. 7).

Example 12

Analysis of the Predicted Amino Acid Sequence of Rat Kidney Synthetase

The deduced amino acid sequence contains all the five independently determined peptide sequences: amino acid residues 14–29, 214–231, 289–293, 393–400, 453–461 shown in FIGS. 1 and 2 (corresponding to SEQ. ID Nos. 3, 4, 2, 1, and 5, respectively). Thus, about 12% of the amino acid residues of the enzyme were independently determined by the Edman procedure. Two potential N-linked glycosylation sites (residues 124 and 171, indicated by asterisks (*) in FIG. 2), and one possible O-linked N-acetylglucosamine addition site (residue 389, indicated by (●) in FIG. 2) are found in the sequence. This enzyme has previously been shown to contain a small amount of carbohydrate. Hydropathy analysis, as described in Kyte, J. and Doolittle, R. F. (1982), *J. Mol. Biol.* 157, 105–132, hereby incorporated by reference, (data not shown) revealed a pattern typical of a water-soluble protein. The calculated amino acid composition is in good agreement with the amino acid analyses of the isolated rat kidney GSH synthetase described in Oppenheimer, L., Wellner, V. P., Griffith, O. W., and Meister, A. (1979), *J. Biol. Chem.* 254, 5184–5190, hereby incorporated by reference (data not shown).

Example 13

Tissue mRNA Expression

Northern blot analysis of the rat tissue mRNA using $^{32}$P labeled GSH synthetase probe revealed a 2.1 kb mRNA band. Rat kidney gave the strongest signal among the tissues examined (heart, brain, spleen, lung, liver, skeletal muscle, kidney, testis) consistent with the finding that kidney exhibits the highest GSH synthetase activity among the various tissues. The intensity of the band found with liver was about 5% of that found in kidney.

This invention provides the first amino acid sequence of GSH synthetase from a mammalian source. The cDNA sequence contains 1905 nucleotides with an open reading frame of 1422 nucleotides coding for 474 amino acid residues. The deduced amino acid sequence leads to molecular weight (52,344) which is not far from previous estimates (55,000) based on SDS gel electrophoresis of isolated rat kidney GSH synthetase. A molecular weight of 55,000 daltons also corresponds with that expected for the recombinant enzyme of the invention when both N-linked sites are glycosylated.

The enzyme was found to have a molecular weight of 118,000 as determined by gel filtration chromatography, suggesting that the rat kidney enzyme is composed of two apparently identical subunits. All of the five independently determined peptide sequences were found in various sections of the cDNA sequence. The data support the conclusion that the two subunits are identical. The GSH synthetases isolated from *Aspergillus niger* ($M_r$ 110,000), described in Murata, K., Kimura, A., and Yajima, N. (1989), *Agri. Biol. Chem.* 53, 1145–1149, hereby incorporated by reference, and bovine erythrocytes (121,000), described in Wendel, A. (1973) in Proceedings of the 16th Conference of the German Society of Biological Chemistry, (Flohé, L., Ben öhr, H. O. Ch., Sies, H., Wallmer, H. D., and Wendel, A. eds.), pp. 69–78 Georg Thieme Publishers Stuttgart, hereby incorporated by reference, also contain two apparently identical subunits.

Computer-aided comparisons of the amino acid sequence of rat kidney GSH synthetase with the sequences of other GSH synthetases in the literature were carried out. Comparisons of the rat enzyme sequence with that of *E. coli*, (Gushima, H., Miya, T., Murata, K., and Kimura, A. (1983), *J. Appl. Biochem.* 5, 210–218, and Gushima, H., Yasuda, S., Soeda, E., Yokota, M., Kondo, M., and Kimura, A. (1984), *Nucl. Acids Res.* 12, 9299–9307), each of which is hereby incorporated by reference, showed no significant similarity. About 30% similarity was found with the yeast enzyme (Mutoh, N., Nakagawa, C. W., Ando, S., Tanabe, K., and Hayashi, Y. (1991), *Biochem Biophys. Res. Comm.* 181, 430–436), and about 65% with the sequence reported for the frog (Habenicht, A., Hille, S., and Knochel, W. (1993), *Biochem. Biophys. Acta* 1174, 295–298), each of which is hereby incorporated by reference.

It was initially believed that glycoproteins are synthesized in the endoplasmic reticulum and Golgi apparatus and delivered to the cell membrane. However, recent evidence indicates that glycoproteins also exist in the cytoplasm, Hart, G. W., Haltiwanger, R. S., Holt, G. D., and Kelly, W. G. (1989), *Annu. Rev. Biochem.* 58, 841–874; Berlin, W. K. and Hanover, J. A. (1993), in *Glycobiology: A Practical Approach* (Fukuda, M. and Kobata, A. eds.) pp. 329–347. The majority of the cytoplasmic glycoproteins are modified by O-linked N-acetylglucosamine, but other types of modification are also present. Isolated rat kidney GSH synthetase is known to contain a small amount (2%) of carbohydrate, as described in Oppenheimer, L., Wellner, V. P., Griffith, O. W., and Meister, A. (1979), *J. Biol. Chem.* 254, 5184–5190. There are two asparagine residues (124 and 171) in the deduced amino acid sequence that fit the requirement for N-linked protein glycosylation: Asn-X-Ser/Thr (X: all amino acid residues except Pro), and one serine residue (389) agrees with the general pattern for an O-linked N-acetylglucosamine addition site (Asp)-Ser/The-$X_n$-Pro. Further study on the significance of the glycosylation of this enzyme is needed.

Knowledge of the amino acid sequence of mammalian GSH synthetase is essential for further studies on the structure, mechanism of action, and physiological function of this enzyme. Such information will be of importance in understanding the biochemical mechanisms associated with GSH synthetase deficiency in humans. Availability of the amino acid sequence of rat kidney GSH synthetase will facilitate the determination of the amino acid sequence of the human enzyme. This may be expected to be valuable for understanding of the biochemical defects associated with human GSH synthetase deficiency, and for development of improved methods for prenatal diagnosis of the human diseases associated with defects in GSH synthetase.

Although the invention has been described in detail for the purpose of illustration, it is understood that such detail is solely for that purpose, and variations can be made therein by those skilled in the art without departing from the spirit and scope of the invention which is defined by the following claims.

What is claimed is:

1. An isolated nucleic acid encoding a glutathione synthetase, wherein said glutathione synthetase has the amino acid sequence of SEQ. ID. No. 6.

2. The isolated nucleic acid according to claim 1, wherein the nucleic acid is a DNA.

3. The isolated nucleic acid according to claim 2, wherein the DNA is a cDNA.

4. The isolated nucleic acid according to claim 1, wherein the nucleic acid is a RNA.

5. The isolated nucleic acid according to claim 4, wherein the RNA is an mRNA.

6. The isolated DNA according to claim 2, wherein the DNA has the nucleotide sequence of SEQ. ID. No. 7.

7. The isolated DNA according to claim 2, wherein the DNA has the nucleotide sequence of SEQ. ID. No. 8.

8. A recombinant expression system comprising an expression vector into which is inserted a heterologous nucleic acid according to claim 1.

9. The recombinant expression system according to claim 8, wherein the nucleic acid is inserted into said vector in proper sense orientation and correct reading frame.

10. A recombinant DNA expression system comprising an expression vector into which is inserted a heterologous DNA according to claim 2.

11. The recombinant DNA expression system according to claim 10, wherein the DNA has the nucleotide sequence of SEQ. ID. No. 7.

12. The recombinant DNA expression system according to claim 10, wherein the DNA has the nucleotide sequence of SEQ. ID. No. 8.

13. The recombinant DNA expression system according to claim 10, wherein the DNA is inserted into said vector in proper sense orientation and correct reading frame.

14. A host cell incorporating a heterologous nucleic acid according to claim 1.

15. The host cell according to claim 14, wherein the cell is a mammalian cell.

16. The host cell according to claim 14, wherein the heterologous nucleic acid is inserted in a recombinant DNA expression system comprising an expression vector.

17. A host cell incorporating a heterologous DNA according to claim 2.

18. The host cell according to claim 17, wherein the DNA has the nucleotide sequence of SEQ. ID. No. 7.

19. The host cell according to claim 17, wherein the DNA has the nucleotide sequence of SEQ. ID. No. 8.

20. The host cell according to claim 17, wherein the heterologous DNA is inserted in a recombinant DNA expression system comprising an expression vector.

* * * * *